United States Patent [19]

Gooch et al.

[11] Patent Number: 5,305,081
[45] Date of Patent: Apr. 19, 1994

[54] BOTTLE STRESS ANALYSIS SYSTEM

[75] Inventors: Jan W. Gooch, Atlanta; James W. Larsen, Douglasville, both of Ga.

[73] Assignee: Constar Plastics Inc., Atlanta, Ga.

[21] Appl. No.: 936,902

[22] Filed: Aug. 27, 1992

[51] Int. Cl.$^5$ .................. G01N 21/21; G01N 21/90
[52] U.S. Cl. ...................... 356/240; 250/223 B; 356/367; 356/428
[58] Field of Search ............ 356/428, 240, 364, 365, 356/366, 367; 250/223 B, 225

[56] References Cited

U.S. PATENT DOCUMENTS

| | | | |
|---|---|---|---|
| 1,934,187 | 11/1933 | Glasgow et al. | 356/33 |
| 3,348,049 | 10/1967 | Stacey | 250/223 B |
| 3,880,524 | 4/1975 | Dill et al. | 250/225 |
| 3,963,348 | 6/1976 | Nakatani et al. | 356/240 |
| 4,304,995 | 12/1981 | Huttenen et al. | 250/223 B |
| 4,547,067 | 10/1985 | Watanabe | 356/33 |
| 4,908,507 | 3/1990 | Imre et al. | 356/240 |
| 5,049,750 | 9/1991 | Hoshino et al. | 250/223 B |

Primary Examiner—Richard A. Rosenberger
Attorney, Agent, or Firm—Locke Reynolds

[57] ABSTRACT

A bottle stress analysis system using polarized light for determining stress levels of a transparent plastic bottle includes a rotation assembly for rotating the bottle. A polarized light source assembly is insertible into the bottle cavity to direct plane polarized light through the bottle wall and an analyzer assembly is positioned outside the bottle for measuring intensity of light passing through the bottle wall. In order to measure changes in polarization, the analyzer assembly has a polarization analyzer positioned to transmit the light to a photodetector. A mechanism for rotating either the polarized light source or the analyzer to determine maximum and minimum polarized light intensity at the photodetector facilitates determination of stress at a plurality of points along the bottle wall. A computer controlled analysis of the polarized light intensity can be used to produce a stress profile of the bottle, permitting rejection of bottles having abnormal internal stress that are likely to fail under internal pressure loading.

17 Claims, 3 Drawing Sheets

BOTTLE STRESS ANALYSIS SYSTEM

BACKGROUND AND SUMMARY OF THE INVENTION

This invention relates to the use of polarized light to determine stress in transparent articles. More particularly, the present invention relates to an apparatus for measuring stress levels present in blown plastic bottles suitable for containing drinks or foods.

Analysis of stress distributions in models composed of transparent materials is commonly employed by engineers to verify calculations of stress concentration in large scale structures. Plane polarized light is directed to pass through transparent plastic models of a structure. As the plane polarized light passes through the model, the light breaks up at every point (birefringence) into two components corresponding to the directions of the two principal stresses at the point. If the light is then passed through another polarizing element (conventionally known as an analyzer), intensity variations or interference bands form that are indicative of principal stresses in the model. This method of stress determination is quite useful because it is non-destructive and can give both quantitative and qualitative information as to stress defects.

Stress determination in plastic bottles used as containers for food or drink is important to reduce failure rates of bottles. Many applications of plastic bottles require subjecting the bottles to high temperatures and pressures, both conditions capable of causing failure in a bottle weakened by a stress concentrating defect. Accordingly, determination of stress at an analysis point on a blown plastic bottle using polarized light and taking advantage of the birefringent properties of aligned polymers and polymeric crystals in blown plastic bottles would be advantageous. Plane polarized light passing through the bottle will travel at different velocities, with light polarized parallel to the optical axis of a polymeric crystal travelling at a different velocity than light polarized perpendicular to the optical axis of the crystal. When the light recombines after passing through the crystal, the light may be circularly, elliptically, or linearly polarized. Since light typically passes through several polymeric crystals as the light travels through the bottle wall, output is commonly elliptically polarized, being a linear function of polarization in the light path through the bottle wall.

The degree of elliptically polarized light passing through the bottle is a function of both the effective thickness and the birefringence of the polymeric crystals in the bottle wall. Changes in polarization are therefore dependent on wall thickness variations as well as stress variations. Since many crystals having differing orientations and birefringent properties are present in a light path, the initial linear polarization is almost destroyed, with a nearly random polarization of the emergent light. However, a small residual polarization typically remains that is indicative of stress and wall thickness variations. The intensity of polarization is measurable, and multiple measurements can be taken at a plurality of analysis points on the bottle wall to ensure consistency of the bottle wall and reduce chance of bottle wall failure.

Accordingly, the present invention provides a bottle stress analysis system using polarized light for determining stress levels of a transparent plastic bottle having a bottle wall that defines a bottle cavity. The bottle stress analysis system includes a rotation assembly for rotating the bottle and a polarized light source assembly insertible into the bottle cavity to direct plane polarized light through the bottle wall. An analyzer assembly is positioned outside the bottle for measuring intensity of light passing through the bottle wall, the analyzer assembly having a polarization analyzer positioned to transmit the light to a photodetector. In addition, a mechanism for rotating one of the polarized light source and the analyzer to determine maximum and minimum polarized light intensity at the photodetector, and consequently measure stress levels at the analysis point, is provided. It will be appreciated that the analysis point may be located at any area of the bottle including the base or finish and is not limited to merely the sidewall of the bottle.

In preferred embodiments the rotation assembly of the bottle stress analysis system includes a rotatable platter configured to support the bottle. A platter stepper motor is connected to the platter to rotate the platter a predetermined angular distance and briefly maintain a stationary position until maximum and minimum polarized light intensity is determined. A computer control assembly for automatically controlling operation of the platter stepper motor is also provided, with the computer control assembly controlling the angular distance through which the platter is rotated, and the duration the stationary position is maintained before further rotation. Motors other than a stepper motor could be used with corresponding control means to achieve substantially the same result.

To effectively provide a source of directed, linearly polarized light, the bottle stress analysis system includes polarized light source assembly. The polarized light source assembly includes a periscope insertible through a neck of the bottle into the bottle cavity, the periscope holding a light source and a polarizer that transmits plane polarized light, with the polarizer being positioned to transmit plane polarized light at a 45° angle with respect to an axis of symmetry of the bottle. The light source can optionally be a light emitting diode (LED) connected to a light source intensity control to vary intensity of light emitted by the LED. A lens (or multiple lens system) for focusing light emitted by the light emitting diode, and a mirror for reflecting converging, plane polarized light toward a stress analysis point on the bottle coincident with the focal point are also positioned in the periscope. To further increase control of the system, the light source intensity control is connected to a computer control assembly for automatically controlling operation of the light source intensity control.

After light has passed from the periscope and through the bottle wall, the bottle stress analysis system utilizes an analyzer assembly for linearly polarizing the light. In addition to a polarizing element (the analyzer) the analyzer assembly includes a lens for focusing polarized light passing through the polarization analyzer onto the photodetector. The photodetector is configured to have a varying electric current in response to variations in light intensity, and further includes an electrical converter for converting the electrical current to an electrical voltage, and an amplifier for amplifying that voltage. A computer control assembly having an analog to digital converter converts this elecrical voltage output of the amplifier into computer readable digital format.

The rotating means for rotating the polarization analyzer includes an analyzer rotation assembly for rotating the polarization analyzer relative to a fixed plane of polarization of light emitted by the polarized light source assembly. An analyzer stepper motor is connected to the polarization analyzer to rotate the polarization analyzer a predetermined angular distance and briefly maintain a stationary position until maximum and minimum polarized light intensity is determined. Again, to increase ease of operation and speed of bottle stress analysis, a computer control assembly for automatically controlling operation of the analyzer stepper motor is provided. The computer control assembly controls the angular distance through which the polarization analyzer is rotated, as well as the duration the stationary position is maintained before further rotation.

The various features and advantages of the invention will become more apparent to those skilled in the art upon consideration of the following detailed description of a preferred embodiment exemplifying the best mode of carrying out the invention as presently perceived.

DETAILED DESCRIPTION OF THE INVENTION

Figure 1:
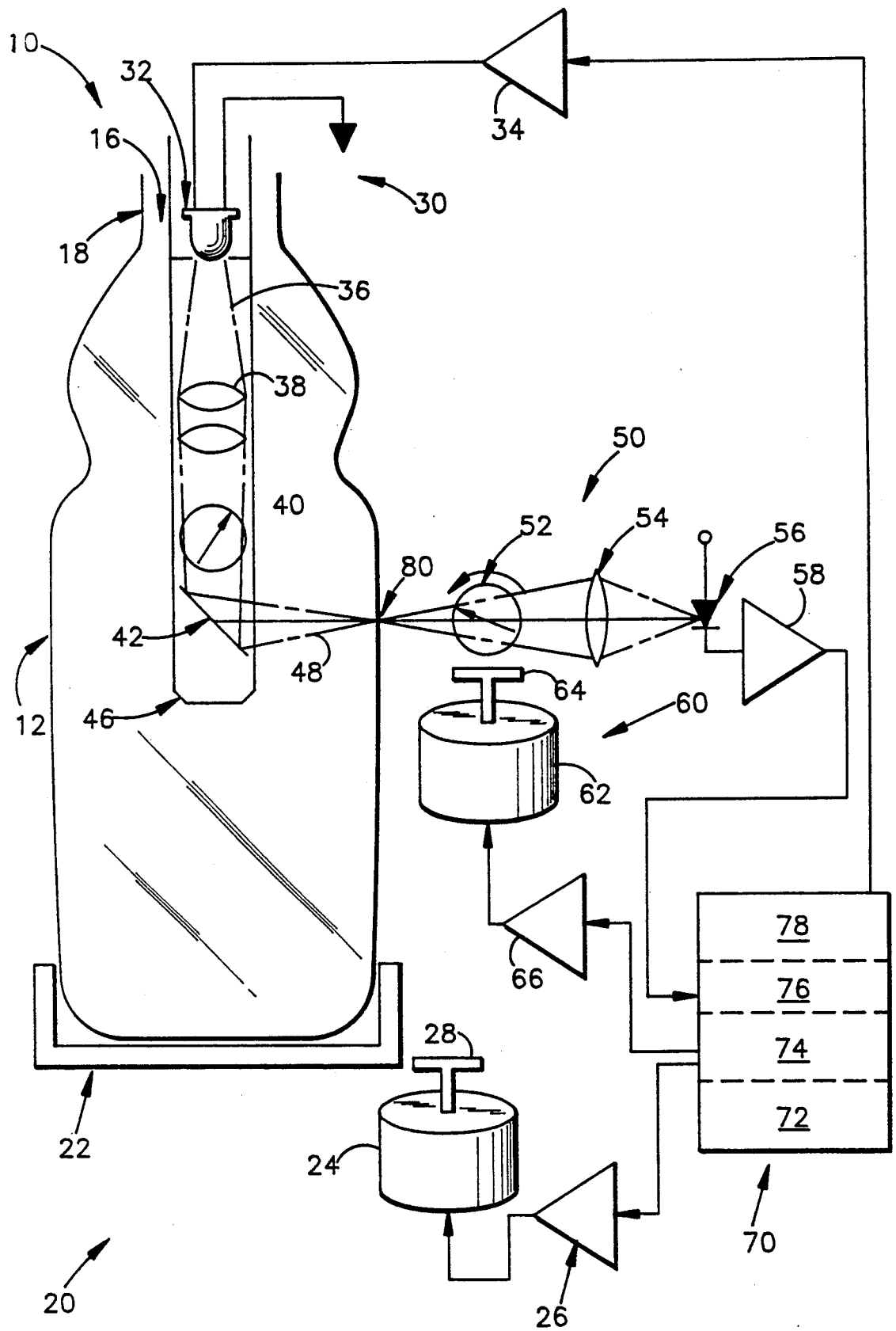
FIG. 1 is a schematic view of a bottle stress analysis system in accordance with the present invention, the bottle stress analysis system including a rotatable platter supporting a bottle through which polarized light is directed and its intensity analyzed.

A bottle stress analysis system 10 as illustrated in FIG. 1 is useful for measuring relative stress level as a function of light polarization changes in light passing through transparent containers such as bottle 12. Bottle 12 is a conventional plastic bottle commonly used to hold, for example, carbonated beverages, purified or mineral waters, or fruit juices. As is readily apparent from the illustration, the bottle 12 has a bottle wall 14 surrounding a bottle cavity 16. Access to the bottle cavity is through a bottle neck 18 that can be easily closed off by a removable plastic screw cap or other sealing mechanism. The bottle 12 is blow mold formed by rapid pneumatic expansion of heated plastic parisons that expand to contact walls of a mold cavity. This method of formation imparts a stress induced crystal alignment to the microscopic polymeric crystals (and long chain polymeric molecules) in the bottle wall.

Aligned polymers and polymeric crystals exhibit a high degree of birefringence. This birefringence causes polarized light to become circularly or elliptically polarized upon passing through the polymeric crystal since light polarized parallel to and perpendicular to the optical axis of a biaxial crystal travels at different velocities. Depending on the thickness of the material, the transmitted light can be circularly, elliptically or linearly polarized. If there is more than one polymeric crystal present in the beam path, the output is the sum of the various degrees of elliptical polarization. The degree of polarization is a function of the effective thickness and birefringence of the crystal. polarization changes measured by the bottle stress analysis system are caused by a combination of the wall thickness variations as well as the stress variations. However, since variations of thickness among the polymeric crystals give many possible degrees of elliptical polarization, and since the number of polymeric crystals in any section through the bottle wall 14 is quite large, total light output not attributable to stress variations in the bottle wall will be approximately randomly polarized.

When a polarized light source assembly 30 is positioned inside the bottle cavity 16 to direct polarized light 48 outward through the bottle wall 14, the light 48 can be directed at 45° to the axis of symmetry of the bottle. Due to the symmetrical flow during molding the light is polarized at 45° to the major optical axis. The average polarization of the light after passing through the bottle is near zero, with the plastic in the bottle has destroyed virtually all of the initial polarization of the light beam. If the bottle were perfectly homogeneous the final polarization angle should be small and constant. The polarization angle change for linearly polarized light is measured by passing the light that is transmitted through the bottle through an analyzer assembly 50 that includes a polarizing analyzer 52. This polarizing analyzer 52 is rotated to determine the maximum and minimum positions of light intensity, and those intensities are quantified. The difference between the maximum and minimum intensities divided by their sum is the calculated polarization. The polarization measured through the bottle divided by the polarization with no bottle present (the initial polarization of the source and source polarizer) is the relative polarization change R. The relative polarization change R is plotted and analyzed for the measured bottle. When measured around the circumference of a bottle, R is not constant, as would be expected for a homogeneous bottle with no substantial stress induced polarization. There are various levels of apparently random fluctuations. This occurs because the bottles are not uniform. Each bottle contains thickness and stress variations caused by the molding process which are the underlying cause of the variations in R.

Annealing of the bottle 12 reduces its residual stress variations, and therefore reduces the fluctuations in R. Stress differences between small areas of the bottle wall 14 (the high spatial frequency differences) are the first to be relieved during annealing. Because a priori calculations of acceptable stress levels based on polarization curves is not possible, the bottle stress analysis system determines a correlation between stress and to observed polarization values. These correlations are established by measuring several bottles at various states during the annealing process. These correlation values are not invariable and should be calibrated for each mold and new batch of resin. However, as a general rule the lower the fluctuations in R the better the annealing of the bottle.

As illustrated in FIG. 1, directing polarized light through the bottle wall 14 is simple and convenient with use of the polarized light source assembly 30. The polarized light source assembly includes a light source 32 conveniently constructed from a red light emitting diode (LED) producing substantially monochromatic light at 660 nanometers. Alternatively, light emitting devices producing monochromatic light between about 450 and 1200 nanometers are acceptable, as are full or continuous spectrum light sources with monochromatic filters. The light source 32 is controlled by a light source intensity control 34 positioned outside the bottle cavity 16. Non-polarized light 36 is emitted by the light source 32, focused by relay lenses 38, and passed through a linear polarizer 40 having an optical axis at 45° with respect to the axis of the bottle 12. The angle 45° is chosen because it tends to reduce the effects of other system errors such as wobble in the mechanical system and misalignment. Other angles from 0° to 360° have been tried and given usefull results. Low cost, general purpose linear photographic polarizers that are useful through the visible light and near infrared spectral regions can be used. Alternatively, nicol prisms or other conventional optical polarizers may be used. The linearly polarized light 48 is reflected off a mirror 42 and directed to a focal point at about the position of the bottle wall 14. After passing through this predetermined analysis point 80 on the bottle wall 14, the light is received by the analyzer assembly 50.

As illustrated in FIG. 1, the light source 32, relay lenses 38, polarizer 40, and mirror 42 are permanently mounted in a periscope 46. The periscope 46 is typically formed from metal or plastic, and has a generally cylindrical construction with a radius sufficiently small to allow its easy insertion through the bottle neck 18 and into the bottle cavity 16. The periscope 46 is formed to define a periscope aperture 44 through which polarized light 48 reflected from mirror 42 can pass toward the bottle wall 14. The periscope 46 is mounted for vertically directed reciprocal motion with respect to a base (not shown), allowing the periscope 46 to be raised and lowered. When the periscope 46 is raised, a bottle 12 to be analyzed for stress can be prepositioned below the periscope 46. Lowering the periscope 46 allows initialization measurements (no bottle present) or polarization measurements (with bottle wall 14 present between the polarized light source assembly 30 and analyzer assembly 50). Raising or lowering of the periscope 46 can be accomplished manually or automatically.

Light passing through the analysis point 80 on the bottle wall 80 is received by the analyzer assembly 50. The analyzer assembly 50 includes a polarizing analyzer 52, a convergently focusing detector lens 54, a photodetector 56 and an amplifier 58. The polarizing analyzer 52 can be of identical construction to the polarizer 40, and like polarizer 40 can be formed from standard, general purpose photographic polarizers. The light passing through this second polarizing analyzer is focused by detector lens 54 onto the photodetector 56. The photodetector is conveniently a large area (typically 0.250 inches in diameter) silicon photodetector having a response curve that covers the emission spectrum of the polarized light and has peak response at approximately 850 nanometers. Typically, the response of such conventional photodetectors is linear with respect to intensity within a few percent and is uniform across its surface. This uniformity reduces the current output changes that are due to position changes of the light image. Easily visible surface irregularities, as well as other variations in the bottle wall, should be avoided when determining an analysis point 80 because such irregularities can cause the image to move on the photodetector, resulting in apparent light intensity changes. The photodetector converts the light to an electrical current, which is then converted to a voltage signal and amplified by the amplifier 58. The Amplifier 58 can also include electronic filters for reducing electronic noise and signal drift.

To determine the maximum and minimum polarized light intensities (which give the amount of rotation of the plane of polarization), the analyzer 52 of the analyzer assembly 50 is rotated with respect to the polarizer 40. An analyzer rotation assembly 50 includes an analyzer stepper motor 62, an analyzer drive link 64, and motor control 66. The stepper motor 62 allows the analyzer to be slightly rotated, held still momentarily for photodetector measurements to be taken, and rotated to a new position for further measurements. By controlling the amount of rotation, the precision of maxima or minima determination can be easily enhanced or decreased.

To change the position of the analysis point 80 the periscope 46 can be raised or lowered to different vertical positions with respect to the bottle wall 14. Alternatively, a series of analysis points can be obtained by rotating the bottle 12 while holding the periscope level constant. As shown in FIG. 1, this is accomplished by positioning the bottle 12 on a rotation assembly 20. The rotation assembly 20 includes a platter 22, a platter stepper motor 24, a motor control 26, and a platter drive link 28. Like the analyzer 52, the platter 22 and the bottle 12 resting upon it can be slightly rotated, held still momentarily for photodetector measurements to be taken, and rotated to a new position for further measurements. By controlling the amount of rotation, the precision of stress determination along a radius of the bottle 12 can be easily enhanced or decreased.

Operation of the bottle stress analysis system 10, reduction of photodetector intensity data, and presentation of stress analysis data for a bottle 12 can be augmented by use of a computer control assembly 70. The computer control assembly 70 includes a conventional electronic computer 72 linked to external signals and machinery by parallel port 74, analog to digital convertor 76, and digital to analog convertor 78. The analog to digital convertor 76 is connected to the amplifier 58 to receive output from photodetector 56. The amplified voltage signal produced by amplifier 58 is converted to a digital signal and passed to the control computer by an analog-to-digital converter board 76. The light intensity data is then processed by the control computer 72. In addition the control computer 72 can control the intensity of the LED output using a digital-to-analog converter to drive the voltage controlled light source intensity control 34. The intensity of the light source 32 is controlled by varying the current. The control computer 72 can also control the rotation of the bottle and the analyzer polarizer by using the stepping motors 26 and 66 coupled to it through the parallel data output port 74.

Analysis of light intensity maxima and minima and display of calculated stress levels can be done with the following exemplary computer program suitable for controlling operation of many conventional personal, mini, and mainframe computer systems. Generally the computer program is subdivided into control and analysis subprograms with the computer controlling initialization and operation of system 10, and analyzing data to present a human readable output showing bottle stress levels. The following program, written in the C language, can be used to control and analyze data produced by the bottle stress analysis system.

```c
/* File BOTAN47S.C last update 03-08-92 at 13:00 */
/* This is a slow version for the first unit: has ledval=1312
   and delttm=20 */
/* adds fft average and slope from 200 to 800 pts/rev */
/* genterated from file BOTAN45.C last update 01-01-92 at 17:30
   by changing to an elliptical region for goodness which is
   read in from the file botgood0.lim */
/* This program controls the bottle annealing time evaluation
   unit (BATE Unit)*/
/* This version finds polarization first with no bottle and then
   runs at the two maxs and two mins. */
/* it is for 45 deg polar */

/*#include <time.h>*/ include <stdio.h>
include <stdlib.h>
#include <math.h>
#include <alloc.h>
#include <dos.h>
#include <conio.h>
#include <graphics.h>
#include <process.h>

/***************************************************/
/******** Trig Constants ***************************/
double SQR2;/*=sqrt(2.0)*/
double SQR51;/*=1.5*(sqrt(5.0)-1)*/
double SQR52;/*=1.5*(3.0-sqrt(5.0)*/
double pi,PI,PI2;

/*********** Fourier transform function **********/
extern int four2(double huge *data,int nn,int isign);
/***************************************************/

/***************************************************/
/********* Spline Display Functions ***************/
extern int flnpr(int n,int ntp,double huge *x,double huge *y,
        double huge *a,double huge *b,
        double huge *x1,double huge *x2,double huge *x3,
        double huge *y1,double huge *y2,double huge *y3);
extern int tridiag(int n,double huge *a,double huge *b,double huge *d)
extern double fcpt(double theta,double phi);
extern double f2dlng(double p1x,double p1y,double p0x,double p0y);
extern double f2darg(double p1x,double p1y,double p0x,double p0y);
/***************************************************/ int trierr;

/*********** ellipitical limits variables *******/
double aeg,beg,aeb,beb;

extern void lsq(int npts);/* least squares parabola fit function */
float xlsf[50],ylsf[50];
float a,b,c,xm,ym;
int minfl;/* 1=max, 0=straight line, -1=min */ extern int adc();
extern void muxset(int mxv);
extern void digout(int dgv);
extern void dacout(int dcv);
unsigned int adadd;/* adc base address*/
unsigned int adast;/* adc start trigger */
unsigned int adalb,adahb;/* adc low and high bytes */
unsigned int adamx;/* acd mux scan channel address*/
```

```c
unsigned int dacl,dach;/* dac low and high bytes */
unsigned int digol,digoh;/* digital output low and high bytes */ extern void polsf();
extern void polsr();
extern void plasf();
extern void plasr();
int plamot;/*platter motor counter*/
int polmot;/*polarizor motor counter*/
int deltm;/*motor step delay time*/
extern float ledoff();
int ledval;/*dac value to drive the LED. The dac is 10 volts and 4096 st
            the LED driver is 5mA/volt. Thus the output is 50/4096 mA
            per step.*/ float sinv[700],cosv[700];
   float savg[50],cavg[50],phase[50],pavg[50],bavg[50];
   float admax[1900],admin[1900],adrat[1900];
   float ratd[1900],ratn[1900],ratf[1900];
   float hf[201];
   int ratb[1800];
   float dat[50];
   float wc;
   int nfp,nfw,k1,k2;

void main()
   {
   struct time now;
   struct date today;
   char flnm[80],flnm1[80];
   FILE *flp;
   FILE *flp1;
   char comm1[80];
   char runnu[80];
   int gdrv,gmod;/*graphics control codes*/
   float TEMP;
   float temp0,temp1,temp2,temp3,temp4,temp5,temp6;
   char cmnd,cmnd1;
   float pfavg,pfsig,pfrsig;
   int ptavg,ptsig;
   int ptmp,ptemp;
   int xpix,xpix1;
   int hg,sg;
float yoff;
int bflg;/* bottle bad flg 0=good 1=marginal 2=bad */
int pdflg;
int msflg;
float gdnf;
double taa;
int mspts;
int gls;
int gsfl;
int igb,jgb,igb0,ige,jge,ige0,jge0;
int ibb,ibe,jbe;
int bdfl,gdfl;
int ngl;
float avgdr;
int nbsp;
float xi,c1,c2,d1,d2,bi,ai;
float avgin,lint0,lint1,lint2;

int i,j,k,kk,l;
float maxval,minval;
int maxx,minx;
float temp;
```

```
char chr;
float polmin,polmax;
int erflg;
int curpos,newpos,maxpos,minpos;
float rat[50];
float pmxavg,pmnavg;
float ledzer;
float avg,avgt,sig,sigt;
float avgpha,sigpha,norfac,norpha;
int nopts;
float setint;/*the desired input adc value=2048+actual data*/
int ndiv;
int psiz,tsiz;/*tsiz=2*psiz+1  tsiz is the # of data pts about max tak
double pi,pi2,theta;
int nsteps;
/******* end of variable list *********/
int nfft;
int sfft;
int nffts;
int nsft;
int nsftl;
int npp;
double ffta1,ffta2,ffta3,fftd1,fftd2,fftb,fftm,fftavg;
double ncyc;
double delt;
double freq1,freq2;
double per;
double mag;
int jjj;

int ncomm;/*number of comments*/ int nst,ntot;

long m;

/************ spline array variables **************/
double huge *x;/*pointer to the array of data points*/
unsigned long xsz;/*size of data array*/
double huge *x1;/*pointer to the array of fft data*/
unsigned long x1sz;/*size of fft array*/
double huge *x2;/*pointer to the array of fft data*/
unsigned long x2sz;/*size of fft array*/
double huge *x3;/*pointer to the array of fft data*/
unsigned long x3sz;/*size of fft array*/
double huge *y;/*pointer to the array of fft data*/
unsigned long ysz;/*size of fft array*/
double huge *y1;/*pointer to the array of fft data*/
unsigned long y1sz;/*size of fft array*/
double huge *y2;/*pointer to the array of fft data*/
unsigned long y2sz;/*size of fft array*/
double huge *y3;/*pointer to the array of fft data*/
unsigned long y3sz;/*size of fft array*/
double huge *a;/*pointer to the array of fft data*/
unsigned long asz;/*size of fft array*/
double huge *b;/*pointer to the array of fft data*/
unsigned long bsz;/*size of fft array*/
double huge *d;/*pointer to the array of fft data*/
unsigned long dsz;/*size of fft array*/ int n,ntp;
int olp;/* overlap in points*/
int ndp,isp;
double npdiv;
double xt,tm,t,res,tdiv;

/************ end of variable list **************/
```

```c
/************ set up data arrays ****************/
xsz=2100;
x=(double huge *)farmalloc(xsz*sizeof(double));
x1sz=2100;
x1=(double huge *)farmalloc(x1sz*sizeof(double));
x2sz=2100;
x2=(double huge *)farmalloc(x2sz*sizeof(double));
x3sz=2100;
x3=(double huge *)farmalloc(x3sz*sizeof(double));
ysz=2100;
y=(double huge *)farmalloc(ysz*sizeof(double));
y1sz=2100;
y1=(double huge *)farmalloc(y1sz*sizeof(double));
y2sz=2100;
y2=(double huge *)farmalloc(y2sz*sizeof(double));
y3sz=2100;
y3=(double huge *)farmalloc(y3sz*sizeof(double));
asz=2100;
a=(double huge *)farmalloc(asz*sizeof(double));
bsz=2100;
b=(double huge *)farmalloc(bsz*sizeof(double));
dsz=8200;
d=(double huge *)farmalloc(dsz*sizeof(double));

/********** read in ellipse axis values **********/
stpcpy(flnm1,"c:\\bottle\\botgood0.lim");
while((flp=fopen(flnm1,"rt"))==NULL)
   {
   printf("!!!!! Limits file BOTGOOD0.LIM is missing !!!!!\n");
   exit(0);
   }
fscanf(flp,"%f",&TEMP);
fgets(comm1,80,flp);
aeg=(double)(TEMP);
fscanf(flp,"%f",&TEMP);
fgets(comm1,80,flp);
beg=(double)(TEMP);
fscanf(flp,"%f",&TEMP);
fgets(comm1,80,flp);
aeb=(double)(TEMP);
fscanf(flp,"%f",&TEMP);
fgets(comm1,80,flp);
beb=(double)(TEMP);
fclose(flp);

/********** set up filter coeficients **********/
pi=3.141592653589795;
pi2=2.0*pi;
nfft=480;
        nfw=200;
        nfp=200;
        wc=pi2/nfp;
        for(i=0;i<nfw;i++)
            {
            hf[i]=(sin(wc*(i-nfw))/(pi*(i-nfw)))*(0.54-0.46*cos(i*pi/r
            }
        hf[nfw]=wc/pi;

for(k=0;k<nfft;k++)
   {
   theta=2.0*pi2*k/nfft;
   sinv[k]=(float)(sin(theta));
   }
for(k=0;k<nfft;k++)
   {
   theta=2.0*pi2*k/nfft;
```

```
    cosv[k]=(float)(cos(theta));
    }
printf("begin\n");

/******** setup adc board addresses ******/
adadd=0x300;/*adc base address*/
adast=adadd+12;
adalb=adadd+4;
adahb=adadd+5;
adamx=adadd+10;

dacl=adadd+4;
dach=adadd+5;

digol=adadd+13;
digoh=adadd+14;

/********* set mux to chan 4 *********/
muxset(4);

/********* zero the digital outputs ********/
digout(0);

/*********** turn on LED **********/
ledval=1312;/*approx 15 ma value to set up */
dacout(ledval);

cmnd1=' ';
cmnd='0';
/*********** enter the command **********/
while ((cmnd!='X')&&(cmnd!='x'))
    {
    printf("        \n");
    printf("Enter Command: T=take data  P=plot  C=calibrate  X=exit\n")
    cmnd=getch();
    printf("%c  ",cmnd);
chr='';

/**********************************************************/
    /***************** Set up to calibrate ******************/
    /********** The LED ***************/
    if ((cmnd=='C')||(cmnd=='c'))
        {
        cmnd=' ';

/********* initialize motor counters *******/
        polmot=0;
        plamot=0;
        deltm=20;
        /*********** adc board tests ************/
        chr=' ';
        while(chr!='x')
            {
            delay(100);
            temp=adc();
            printf("value=%f  'x'=EXIT\n",temp);
            if(kbhit()!=0)
                {
                chr=getch();
                if(chr=='n') dacout(ledval);
                if(chr=='f') dacout(0);
```

```
            )
          )
/*    i=0;
      chr=' ';
      while(chr!='x')
          {
          delay(100);
          dacout(i);
          temp=50.0*i/4096.0;
          printf("LED cur=%f\n",temp);
          i=i+1;
          if(i>4095) i=0;
          if(kbhit()!=0)
              {
              chr=getch();
              }
          }
*/
/*    i=0;
      chr=' ';
      while(chr!='x')
          {
          delay(1);
          digout(i);
          i=i+1;
          if(i>4095) i=0;
          if(kbhit()!=0)
              {
              chr=getch();
              }
          }
*/
/********** end adc board tests **********/

/********** steping motors tests *********/
/*    printf("stepping motor tests\n");
      chr='f';
      while(chr!='x')
          {
          for(l=0;l<8;l++)
              {
              delay(deltm);
              if(chr=='f')
                  {
                  polsf();
                  plasf();
                  }
              if(chr=='r')
                  {
                  polsr();
                  plasr();
                  }
              if(kbhit()!=0)
                  {
                  chr=getch();
                  }
              }
          }
      digout(0);
*/
/******** end stepping motor tests *******/
          }
/**************************************************************/
/*********** Set up for file to save bottle data ***********/
```

```c
/********** Then take and save bottle data ***************/
if ((cmnd=='T')||(cmnd=='t'))
{
cmnd=' ';

/********* initialize motor counters ********/
   polmot=0;
   plamot=0;
   deltm=20;

/*********** Set up for file to hold bottle data***********/
   chr=' ';
   while((chr!='y')&&(chr!='Y'))
      {
      printf("Enter Bottle Number <4 chars>:");
      scanf("%s",flnm);
      stpcpy(flnm1,flnm);
      gets(runnu);
      printf("Enter run number <3 digits>:");
      gets(runnu);
      strcat(flnm1,runnu);
      strcat(flnm1,".dat");
      printf(" Is %s the correct file name?<Y/N>\n",flnm1);
      chr=' ';
      while(((chr!='y')&&(chr!='Y'))&&((chr!='n')&&(chr!='N')))
         {
         chr=getch();
         }
      }
   chr=' ';
   while((flp=fopen(flnm1,"rt"))!=NULL)
      {
      printf("!!!!! Bottle # and Run # already exist !!!!!!\n");
      chr=' ';
      while((chr!='y')&&(chr!='Y'))
         {
         printf("Enter Bottle Number <4 chars>:");
         scanf("%s",flnm);
         stpcpy(flnm1,flnm);
         gets(runnu);
         printf("Enter run number <3 digits>:");
         gets(runnu);
         strcat(flnm1,runnu);
         strcat(flnm1,".dat");
         printf(" Is %s the correct file name?<Y/N>\n",flnm1);
         chr=' ';
         while(((chr!='y')&&(chr!='Y'))&&((chr!='n')&&(chr!='N')))
            {
            chr=getch();
            }
         }
      chr=' ';
      } flp=fopen(flnm1,"w+t");
   /********** save defect data ***********/
   fprintf(flp,"Bottle Number:%s\n",flnm);
   fprintf(flp,"Run Number:%s\n",runnu);
   gettime(&now);
   getdate(&today);
   fprintf(flp,"Date %02d-%02d-%04d\n",
           today.da_mon,today.da_day,today.da_year);
   fprintf(flp,"Time %02d:%02d:%02d.%02d\n",
           now.ti_hour,now.ti_min,now.ti_sec,now.ti_hund);
   printf("Enter number of comment lines:");
```

```c
        scanf("%f",&TEMP);
        gets(comm1);
        l=(int)(TEMP);
        fprintf(flp,"%d\n",l);
        for (k=1;k<=l;k++)
           {
           printf("line %d:",k);
           gets(comm1);
           fprintf(flp,"%s\n",comm1);
           }
        fprintf(flp,"\n");

/**********************************************/
/**************** start of analysis ***************/

/**************** find phase ****************/
   printf("finding phase\n");
   i=0;
   savg[i]=0;
   cavg[i]=0;
   pavg[i]=0;
   bavg[i]=0;
   for(kk=0;kk<4;kk++)
      {
      /***** turn off the LED and take data ****/
      delay(20);
      bavg[i]=bavg[i]+ledoff();
      for(j=0;j<480;j++)
         {
         delay(10);
         temp=0;
         for(k=0;k<10;k++)
            {
            delay(1);
            temp=temp+(float)(adc());
            }
         temp=temp/10.0;
         pavg[i]=pavg[i]+temp;
         savg[i]=savg[i]+sinv[j]*temp;
         cavg[i]=cavg[i]+cosv[j]*temp;
         polsf();
         }
      /***** turn off the LED and take data ****/
      delay(20);
      bavg[i]=bavg[i]+ledoff();
      }
   bavg[i]=bavg[i]/8.0;
   pavg[i]=pavg[i]/1920;
   pavg[i]=pavg[i]-bavg[i];
   savg[i]=savg[i]/960;
   cavg[i]=cavg[i]/960;
   phase[i]=atan2(savg[i],cavg[i]);
/* printf("back=%f  cdavg=%f\n",bavg[i],pavg[i]);*/
/* printf("sin=%f  cos=%f\  phase=%f\n",savg[i],cavg[i],phase[i]);*/
   rat[i]=sqrt(savg[i]*savg[i]+cavg[i]*cavg[i])/pavg[i];
/* printf("rat[%3d]=%f\n",i,rat[i]);*/
   phase[i]=phase[i]*90.0/pi;/* phase of 2 theta in degrees*/
   phase[i]=phase[i]/0.75;/* phase in steps*/
   if(phase[i]<10)
      {
      nsteps=(int)(10.5-phase[i]);
      for(j=0;j<nsteps;j++) /* step back 10 steps beyond the max */
         {
         delay(deltm);
```

```
            polsr();
            }
        for(j=0;j<10;j++) /* then step 10 steps forward to max */
            {
            delay(deltm);
            polsf();
            }
        }
    else /* it is >=10 steps then just step */
        {
        nsteps=(int)(0.5+phase[i]);
        for(j=0;j<nsteps;j++)
            {
            delay(deltm);
            polsf();
            }
        }
/************************* end find max *********************/
/************** the polarizor is now sitting on the max ********/

/*********** calibrate LED **********/
    printf("calibrating LED\n");
    ledval=820;/*about 10mA*/
    dacout(ledval);

erflg=1;
    while(erflg==1)/* check a span until it is uniform*/
        {
        avg=0;
        for(i=0;i<11;i++) /*take data over 10 degrees*/
            {
            dat[i]=0;
            for(j=0;j<8;j++)
                {
                delay(deltm);
                dat[i]=dat[i]+(float)(adc());
                }
            avg=avg+dat[i];
            for(j=0;j<5;j++)/*move 1deg(5 steps)*/
                {
                delay(deltm);
                plasf();
                }
            }
        avg=avg/11;

erflg=0;
        for(i=0;i<11;i++)
            {
            if(abs((dat[i]-avg)/avg)>0.1) erflg=1;
            }
        }/* the current span is uniform*/ for(i=0;i<7;i++)/* mov back to the 3 deg mark*/
        {
        for(j=0;j<5;j++)/*move 1deg(5 steps)*/
            {
            delay(deltm);
            plasr();
            }
        }
    for(i=0;i<2;i++)/* mov forward to the 5 deg mark*/
        {
        for(j=0;j<5;j++)/*move 1deg(5 steps)*/
            {
            delay(deltm);
```

```
            plasf();
            )
    )

ledval=2048;/*about 25mA*/
    dacout(ledval);
    delay(20);
    setint=2048+1500;
    ndiv=1024;
    erflg=1;
    while((erflg==1)&&(ndiv>1))/* adjust ledval until adc()=setint*/
        (
        temp=0;
        for(j=0;j<8;j++)
            (
            delay(deltm);
            temp=temp+(float)(adc());
            )
        temp=temp/8.0;
        if(abs(temp-setint)<10)
            (
            erflg=0;
            )
            else
            (
            if((temp-setint)>0) ledval=ledval-ndiv;
            if((temp-setint)<0) ledval=ledval+ndiv;
            dacout(ledval);
            delay(20);
            ndiv=ndiv/2;
            )
        )
    printf("ledval=%d  data=%f\n",ledval,temp-2048.0);
    if(abs(temp-setint)>20)
        (
        printf("!!!!! ERROR IN LED LIGHT SOURCE CALIB. !!!!!\n");
        printf("   calib tmp=%f setint=%f\n",temp,setint);
        fflush(flp);
        fclose(flp);
        exit(0);
        )
/*********** end LED calibration ***********/
/*********** polarizor is still on the max ******/

/********************************************/
/******* go into actual data taking ********/
/********************************************/

/******** take no bottle background data ***********/
/******** and re-find the maximum ******************/
printf("first background\n");
i=0;
savg[i]=0;
cavg[i]=0;
pavg[i]=0;
bavg[i]=0;
for(kk=0;kk<4;kk++)
    (
    /******* turn off the LED and take data ******/
    delay(20);
    bavg[i]=bavg[i]+ledoff();
    for(j=0;j<480;j++)
        (
```

```c
            delay(10);
            temp=0;
            for(k=0;k<10;k++)
                {
                delay(1);
                temp=temp+(float)(adc());
                }
            temp=temp/10.0;
            pavg[i]=pavg[i]+temp;
            savg[i]=savg[i]+sinv[j]*temp;
            cavg[i]=cavg[i]+cosv[j]*temp;
            polsf();
            }
        /****** turn off the LED and take data ******/
        delay(20);
        bavg[i]=bavg[i]+ledoff();
        }
    bavg[i]=bavg[i]/8.0;
    pavg[i]=pavg[i]/1920;
    pavg[i]=pavg[i]-bavg[i];
    savg[i]=savg[i]/960;
    cavg[i]=cavg[i]/960;
    phase[i]=atan2(savg[i],cavg[i]);
/*  printf("back=%f   cdavg=%f\n",bavg[i],pavg[i]);*/
/*  printf("sin=%f  cos=%f\  phase=%f\n",savg[i],cavg[i],phase[i]);*/
    rat[i]=sqrt(savg[i]*savg[i]+cavg[i]*cavg[i])/pavg[i];
/*  printf("rat[%3d]=%f   pavg=%f\n",i,rat[i],pavg[i]);*/
    phase[i]=phase[i]*90.0/pi;/* phase of 2 theta in degrees*/
    phase[i]=phase[i]/0.75;/* phase in steps*/
    if(phase[i]<10)
        {
        nsteps=(int)(10.5-phase[i]);
        for(j=0;j<nsteps;j++) /* step back 10 steps beyond the max */
            {
            delay(deltm);
            polsr();
            }
        for(j=0;j<10;j++) /* then step 10 steps forward to max */
            {
            delay(deltm);
            polsf();
            }
        }
        else/* it is >=10 steps then just step */
        {
        nsteps=(int)(0.5+phase[i]);
        for(j=0;j<nsteps;j++)
            {
            delay(deltm);
            polsf();
            }
        }
    delay(deltm);
    bavg[3]=bavg[3]+ledoff();

for(j=0;j<120;j++)/* move polar 120 steps=90 deg to min */
        {
        delay(deltm);
        polsf();
        }

/****** get the second min ************/ printf("second min\n");
    /**** turn off the LED and take data ****/
    delay(deltm);
```

```
bavg[4]=ledoff();

for(i=0;i<=1800;i++) /* take max measurements around the bottle*/
   {
   delay(10);
   temp=0;
   for(k=0;k<10;k++)
       {
       delay(1);
       temp=temp+(float)(adc());
       }
   temp=temp/10.0;
   admin[i]=admin[i]+temp;
   plasf();
   }
/******* end take data ******/
bavg[4]=bavg[4]+ledoff();

/** end of take data loop ****/ printf("REMOVE BOTTLE--press 'g'when ready \n");
chr=' ';
while(chr!='g')
   {
   sound(1600);
   delay(300);
   nosound();
   delay(200);
   if(kbhit()!=0)
       {
       chr=getch();
       }
   }

/******** take no bottle background data ***********/
/******** and refind the maximum ******************/
printf("last background\n");
i=5;
savg[i]=0;
cavg[i]=0;
pavg[i]=0;
bavg[i]=0;
for(kk=0;kk<4;kk++)
   {
   /***** turn off the LED and take data ****/
   delay(20);
   bavg[i]=bavg[i]+ledoff();
   for(j=0;j<480;j++)
       {
       delay(10);
       temp=0;
       for(k=0;k<10;k++)
           {
           delay(1);
           temp=temp+(float)(adc());
           }
       temp=temp/10.0;
       pavg[i]=pavg[i]+temp;
       savg[i]=savg[i]+sinv[j]*temp;
       cavg[i]=cavg[i]+cosv[j]*temp;
       polsf();
       }
   /***** turn off the LED and take data ****/
   delay(20);
   bavg[i]=bavg[i]+ledoff();
```

```
        }
    bavg[i]=bavg[i]/8.0;
    pavg[i]=pavg[i]/1920;
    pavg[i]=pavg[i]-bavg[i];
    savg[i]=savg[i]/960;
    cavg[i]=cavg[i]/960;
    phase[i]=atan2(savg[i],cavg[i]);
/*  printf("back=%f  cdavg=%f\n",bavg[i],pavg[i]);*/
/*  printf("sin=%f  cos=%f\  phase=%f\n",savg[i],cavg[i],phase[i]);*/
    rat[i]=sqrt(savg[i]*savg[i]+cavg[i]*cavg[i])/pavg[i];
/*  printf("rat[%3d]=%f  pavg=%f\n",i,rat[i],pavg[i]);*/

/******** calc ratios and statistics ********/ avg=0;
    sig=0;
    norfac=0.5*(rat[0]+rat[5]);
/*  printf("norfac=%f\n",norfac);*/
    for(i=0;i<1800;i++) /* calculate statistics */
        {
        admax[i]=0.5*admax[i]-0.25*(bavg[1]+bavg[3]);
        admin[i]=0.5*admin[i]-0.25*(bavg[2]+bavg[4]);
        adrat[i]=(admax[i]-admin[i])/(admax[i]+admin[i]);
        adrat[i]=adrat[i]/norfac;
        avg=avg+adrat[i];
        sig=sig+adrat[i]*adrat[i];
        }
    avg=avg/1800.0;
    sig=sqrt((sig-1800.0*avg*avg)/1800.0);
/*  printf("avg=%f  sig=%f\n",avg,sig);*/
    nopts=1800;
/*  printf("nopts=%d\n",nopts);*/
/*  printf("norfac=%f\n",norfac);*/
    fprintf(flp,"nopts=%d\n",nopts);
    fprintf(flp,"norfac=%f\n",norfac);
    fprintf(flp,"avg=%f  sig=%f\n",avg,sig);

avgt=avg;
    sigt=sig;
/*  printf("avgt=%f  sigt=%f\n",avgt,sigt);*/
    avg=0;
    sig=0;
    nopts=0;
    for(i=0;i<1800;i++) /* calculate statistics */
        {
        if((fabs(adrat[i]-avgt))<(2.5*sigt))
            {
            nopts=nopts+1;
            avg=avg+adrat[i];
            sig=sig+adrat[i]*adrat[i];
            }
            else
            {
/*          printf("i=%3d abs(r-av)=%f 2.5sig=%f\n",
            i,fabs(adrat[i]-avgt),2.5*sigt);*/
            }
        }
    avg=avg/nopts;
    sig=sqrt((sig-nopts*avg*avg)/nopts);
/*  printf("avg=%f  sig=%f\n",avg,sig);*/
```

```c
/*  printf("nopts=%d\n",nopts);*/
/*  printf("norfac=%f\n",norfac);*/
    fprintf(flp,"nopts=%d\n",nopts);
    fprintf(flp,"norfac=%f\n",norfac);
    fprintf(flp,"avg=%f  sig=%f\n",avg,sig);

avgt=avg;
    sigt=sig;
/*  printf("avgt=%f  sigt=%f\n",avgt,sigt);*/
    avg=0;
    sig=0;
    nopts=0;
    for(i=0;i<1800;i++) /* calculate statistics */
        {
        if((fabs(adrat[i]-avgt))<(2.5*sigt))
            {
            nopts=nopts+1;
            avg=avg+adrat[i];
            sig=sig+adrat[i]*adrat[i];
            }
            else
            {
/*          printf("i=%3d abs(r-av)=%f 2.5sig=%f\n",
                i,fabs(adrat[i]-avgt),2.5*sigt);*/
            }
        }
    avg=avg/nopts;
    sig=sqrt((sig-nopts*avg*avg)/nopts);
/*  printf("nopts=%d\n",nopts);*/
/*  printf("norfac=%f\n",norfac);*/
/*  printf("avg=%f  sig=%f  relsig=%f\n",avg,sig,sig/avg);*/
    fprintf(flp,"nopts=%d\n",nopts);
    fprintf(flp,"norfac=%f\n",norfac);
    fprintf(flp,"avg=%f  sig=%f  relsig=%f\n",avg,sig,sig/avg);

/************** save data to the file **************/
    printf("Saving data to file\n");
    fprintf(flp,"%f   start light intensity\n",pavg[0]);
    fprintf(flp,"%f   end light intensity\n",pavg[5]);

fprintf(flp," i     max          min         rat\n");
    for(i=0;i<1800;i++)
        {
        fprintf(flp,"%3d %12.6f %12.6f %10.6f\n",
                i,admax[i],admin[i],adrat[i]);
        }
    fprintf(flp,"%d   :# of pts\n",nopts);
    fprintf(flp,"%f   :no bottle polarization\n",norfac);
    fprintf(flp,"%f   :average\n",avg);
    fprintf(flp,"%f   :sigma\n",sig);
    fprintf(flp,"%f   :relative sigma(sig/avg)\n",sig/avg);
    fflush(flp);
    fclose(flp);
    cmnd1='n';/*set cmnd1 to 'n'=new so that data will be plotted*/
    }

/*********************************************************/
/***************** Set up to plot data *****************/
/*********************************************************/
    if (((cmnd=='P')||(cmnd==
    'p'))||(cmnd1=='n'))
        {
```

```c
if((cmnd=='P')||(cmnd=='p'))/* get data from a file*/
    {
    /******* Set up file to read bottle data******/
    printf("Enter Bottle Number <4 chars>:");
    scanf("%s",flnm);
    stpcpy(flnm1,flnm);
    gets(runnu);
    printf("Enter run number <3 digits>:");

gets(runnu);
strcat(flnm1,runnu);
strcat(flnm1,".dat");
while((flp=fopen(flnm1,"rt"))==NULL)
    {
    printf("!!!!! Bottle # and Run # do not exist !!!!!\n");
    printf("Enter Bottle Number <4 chars>:");
    scanf("%s",flnm);
    stpcpy(flnm1,flnm);
    gets(runnu);
    printf("Enter run number <3 digits>:");
    gets(runnu);
    strcat(flnm1,runnu);
    strcat(flnm1,".dat");
    }
    }
if(cmnd1=='n')
    {
    flp=fopen(flnm1,"rt");
    cmnd1=' ';
    }
/*********** read bottle data *************/
printf("\n");
printf("\n");
printf("\n");
printf("\n");
printf("*********** Bottle Data **********\n");
fgets(flnm,80,flp);
printf("%s",flnm);
flnm[18]=0;
fgets(runnu,80,flp);
printf("%s",runnu);
runnu[14]=0;
fgets(comm1,80,flp);
printf("%s",comm1);
fgets(comm1,80,flp);
printf("%s",comm1);
fscanf(flp,"%f",&TEMP);
fgets(comm1,80,flp);
l=(int)(TEMP);
printf("Number of comment lines:%d\n",l);
for (k=1;k<=l;k++)
    {
    fgets(comm1,80,flp);
    printf("%s",comm1);
    }
fgets(comm1,80,flp);

fgets(comm1,80,flp);
fgets(comm1,80,flp);
fgets(comm1,80,flp);
fgets(comm1,80,flp);
fgets(comm1,80,flp);
fgets(comm1,80,flp);
fgets(comm1,80,flp);
fgets(comm1,80,flp);
fgets(comm1,80,flp);
fscanf(flp,"%f",&temp1);
```

```c
            fgets(comm1,80,flp);
            lint1=temp1;
            fscanf(flp,"%f",&temp0);
            fgets(comm1,80,flp);
            lint2=temp0;
            fgets(comm1,80,flp);

/************* FFT and spline constants *************/
    SQR2=sqrt(2.0);
    SQR51=1.5*(sqrt(5.0)-1);
    SQR52=1.5*(3.0-sqrt(5.0));
    PI2=6.28318530717959;
    PI=3.141592653589795;
    pi=PI;

n=1799;
    olp=100;
    ndp=4096;
    npdiv=n+1;
    npdiv=npdiv/ndp;

for(i=0;i<1800;i++)
            {
                fscanf(flp,"%d %f %f %f",&temp0,&temp1,&temp2,&temp3);
                fgets(comm1,80,flp);
                admax[i]=temp1;
                admin[i]=temp2;
                adrat[i]=temp3;

*(x+i)=0.2*i;
                *(y+i)=temp3;

/*              printf("i=%d rat=%f\n",i,adrat[i]);*/
            } fscanf(flp,"%f",&temp0);
            fgets(comm1,80,flp);
            nopts=(int)(temp0);
            fscanf(flp,"%f",&temp1);
            fgets(comm1,80,flp);
            norfac=temp1;
            fscanf(flp,"%f",&temp0);
            fgets(comm1,80,flp);
            pfavg=temp0;
            fscanf(flp,"%f",&temp1);
            fgets(comm1,80,flp);
            pfsig=temp1;
            fscanf(flp,"%f",&temp1);
            fgets(comm1,80,flp);
            pfrsig=temp1;
            printf("2.5 sig removal  nopts=%d\n",nopts);
            printf("     avg=%f    sig=%f    relsig=%f\n",pfavg,pfsig,pfr
            msflg=0;

/************* FFT spectrum calculations *************/
    for (k=0;k<=(n+2*olp);k++)
        {
        *(a+k)=1.0;
        *(b+k)=1.0;
        *(x+k)=k;
        } for (k=0;k<=n;k++)
        {
        *(y+n+olp-k)=*(y+n-k);
        }
```

```
for (k=0;k<olp;k++)
    {
    *(y+k)=*(y+n+1+k);
    *(y+n+olp+1+k)=*(y+olp+k);
    } ntp=1;
trierr=flnpr(n+2*olp,ntp,x,y,a,b,x1,x2,x3,y1,y2,y3);

res=0.000001;
isp=olp;
for(k=0;k<=ndp;k++)
    {
    tm=k*npdiv;
    if(tm>(-*(x+olp)+*(x+isp+1)))
        {
        isp=isp+1;
        }
    t=.5;
    tdiv=.5;
    while(tdiv>=res)
        {
        tdiv=tdiv/2;
        xt=-*(x+olp)+*(x+isp)+t*(*(x1+isp)+t*(*(x2+isp)+t**(x3+isp)));
        if(xt>tm)
            {t=t-tdiv;}
            else{t=t+tdiv;}
        }
    xt=-*(x+olp)+*(x+isp)+t*(*(x1+isp)+t*(*(x2+isp)+t**(x3+isp)));
    *(d+2*k)=*(y+isp)+t*(*(y1+isp)+t*(*(y2+isp)+t**(y3+isp)));
    *(d+2*k+1)=0.0;
/*    fprintf(flp1,"k=%3d x=%f xcal=%f ycal=%f,%f\n",
            k,tm,xt,*(d+2*k),*(d+2*k+1));
*/    } printf("Calculating FFT\n");

/*    fprintf(flp1," freqency(Hz)    real pt    ");

fprintf(flp1," imagenary pt  magnitude\n");
*/        nfft=ndp;
    sfft=1;/*1 means do FFT */
    four2(d,nfft,sfft);

i=0;
    mag=sqrt((*(d+2*i))*(*(d+2*i))+(*(d+2*i+1))*(*(d+2*i+1)));
/*        fprintf(flp1," %11.5f  %11.4e  %11.4e  %11.4e\n",
            i*npdiv,*(d+2*i),*(d+2*i+1),mag/nfft);
*/
    for (i=1;i<(nfft/2);i++)
        {
        mag=sqrt((*(d+2*i))*(*(d+2*i))+(*(d+2*i+1))*(*(d+2*i+1)));
/*        fprintf(flp1," %11.5f  %11.4e  %11.4e  %11.4e\n",
            i*npdiv,*(d+2*i),*(d+2*i+1),mag/nfft);*/
        }
        /********** calc fft slope and avg from 200 to 800 ******/
        ffta1=0.0;
        ffta2=0.0;
        ffta3=0.0;
        fftd1=0.0;
        fftd2=0.0;
        for (i=200;i<=800;i++)
            {
            mag=sqrt((*(d+2*i))*(*(d+2*i))+(*(d+2*i+1))*(*(d+2*i+1)))/nf
            mag=20.0*log10(mag);
            ffta1=ffta1+(double)(i)*(double)(i);
```

```
        ffta2=ffta2+i;
        ffta3=ffta3+1;
        fftd1=fftd1+i*mag;
        fftd2=fftd2+mag;
        }
/*    printf("a1,a2,a3=%g %g %g\n",ffta1,ffta2,ffta3);
    printf("d1,d2=%g %g\n",fftd1,fftd2);*/
    fftb=(ffta2*fftd1-ffta1*fftd2)/(ffta2*ffta2-ffta1*ffta3);
    fftm=(fftd1-ffta2*fftb)/ffta1;
    fftavg=500.0*fftm+fftb;
    printf("fftm=%f  b=%f   mpt=%f  avg=%f\n",
           fftm,fftb,fftavg,fftd2/ffta3);

/****** calculate avg int and i0 ********/
    c1=0;
    for(i=0;i<1800;i++)
       {
       xi=0.5*(admax[i]+admin[i]);
       ratn[i]=xi;
       c1=c1+xi;
       }
    avgin=c1/1800.0;
    printf("bkint1=%f  bkint2=%f\n",lint1,lint2);
    lint0=0.5*(lint1+lint2);
    printf("int0=%f  avgint=%f  reldif=%f\n",
           lint0,avgin,(lint0-avgin)/lint0);
/*     printf("Data Intensity Scaled\n");
    for(i=0;i<1800;i++)
       {
       adrat[i]=adrat[i]*(lint0-avgin)/(lint0-ratn[i]);
       }
*/

/****** calculate the slope ******/
    ratd[0]=adrat[1]-adrat[1799];
    for(i=1;i<1799;i++)
       {
       ratd[i]=adrat[i+1]-adrat[i-1];
       }
    ratd[1799]=adrat[0]-adrat[1798];

/****** clasify points with bad slope ******/
    nbsp=0;
    for(i=0;i<1800;i++)
       {
       if(fabs(ratd[i])>0.005)
          {ratb[i]=1; nbsp=nbsp+1;}
          else{ratb[i]=0;}
       }
    printf("# of bad slope pts=%d\n",nbsp);
    pdflg=0;
    if(nbsp>20) { pdflg=1; }

/****** Find first good section >=gls ******/
    gls=20;
    igb0=0;
    gsfl=0;
    i=0;
    ngl=0;
    while((gsfl==0)&&(i<1800))
       {
       if(ratb[i]==0)
          {
          ngl=ngl+1;
```

```
            )
         else(
         ngl=0;
         )
      if(ngl>=gls)
         (
         gsfl=1;
         igb0=i-ngl+1;
         )
      i=i+1;
      )
/**** now igb0 is the first pt of a section and gsfl=1 ****/

/******* now calc ratn[i] and eliminate bad points *****/
for(i=igb0;i<(igb0+1800);i++)
   (
   if(i>=1800)
      ( j=i-1800; )
      else ( j=i; )

if(gsfl==1) /** on good section **/
      (
      if(ratb[j]==0)
         (
         ratn[j]=adrat[j];
         ige0=i;
         jge0=j;
         )
         else
         (
         gsfl=0;
         ibb=i; ibe=i;
         bdfl=1;
         gdfl=0;
         if(i==(igb0+1799))
            (
            ratn[j]=0.5*(ratn[igb0]+ratn[jge0]);
            )
         )
      )
   if(gsfl==0) /** not on good section **/
      (
      if(bdfl==1)
         (
         if(ratb[j]==1) /* still bad */
            (
            ibe=i;
            if(i>=(igb0+1799))
               (
               for(k=ibb;k<(igb0+1800);k++)
                  (
                  if(k>=1800)
                     ( j=k-1800; )
                     else ( j=k; )
                  ratn[j]=ratn[jge0]+(k-ige0)
                     *(ratn[igb0]-ratn[jge0])/(igb0+1800-ige0
                  )
               )
            )
            else
            (
            gdfl=1; bdfl=0;
            igb=i;
            jgb=j;
            ige=i;
            jge=j;
```

```
            )
        }
    if(gdfl==1)
        { if(ratb[j]==0) /* still good */
            {
            ige=i; jge=j;
            if((ige+1-igb)>=gls) /* now have another good sec
                {
                for(k=igb;k<=ige;k++)
                    {
                    if(k>=1800)
                        { j=k-1800; }
                        else { j=k; }
                    ratn[j]=adrat[j];
                    }
                for(k=ibb;k<igb;k++)
                    {
                    if(k>=1800)
                        { j=k-1800; }
                        else { j=k; }
                    ratn[j]=ratn[jge0]
                        +(k-ige0)*(ratn[jgb]-ratn[jge0])/(igb-ig
                    )
                gsfl=1;
                ige0=i; jge0=j;
                }
            if(i>=(igb0+1799)) /* if now at end */
                {
                for(k=igb;k<=(igb0+1799);k++)
                    {
                    if(k>=1800)
                        { j=k-1800; }
                        else { j=k; }
                    ratn[j]=adrat[j];
                    }
                for(k=ibb;k<igb;k++)
                    {
                    if(k>=1800)
                        { j=k-1800; }
                        else { j=k; }
                    ratn[j]=ratn[jge0]
                        +(k-ige0)*(ratn[jgb]-ratn[jge0])/(igb-ig
                    )
                }
            )
        else /* now it is bad again */
            {
            gdfl=0; bdfl=1;
            if(i>=(igb0+1799))
                {
                for(k=ibb;k<(igb0+1800);k++)
                    {
                    if(k>=1800)
                        { j=k-1800; }
                        else { j=k; }
                    ratn[j]=ratn[jge0]+(k-ige0)
                        *(ratn[igb0]-ratn[jge0])/(igb0+1800-ige0
                    )
                    }
                }
            }
        }
    )
/******** now have ratn[i] ********/
```

```c
avg=0;
sig=0;
for(i=0;i<1800;i++) /* calculate statistics */
    {
    avg=avg+ratn[i];
    sig=sig+ratn[i]*ratn[i];
    }
avg=avg/1800.0;
sig=sqrt((sig-1800.0*avg*avg)/1800.0);
nopts=1800;
printf("Defect Removal  nopts=%d\n",nopts);
printf("       avg=%f  sig=%f  relsig=%f\n",avg,sig,sig/avg);
avgdr=avg;
gdnf=sig;
mspts=0;
for(i=0;i<1800;i++)
    {
    if(fabs(ratn[i]-avgdr)>0.060) { mspts=mspts+1; }
    }
if(mspts>30) { msflg=1;} for(i=0;i<1800;i++)
            {
            ratf[i]=hf[nfw]*ratn[i];
            for(j=0;j<nfw;j++)
                {
                k1=i+j-nfw;
                k2=i-j+nfw;
                if(k1<0) {k1=k1+1800;}
                if(k2>=1800) {k2=k2-1800;}
                ratf[i]=ratf[i]+hf[j]*(ratn[k1]+ratn[k2]);
                }
            }
avg=0;
sig=0;
for(i=0;i<1800;i++) /* calculate statistics */
    {
    avg=avg+ratf[i];
    sig=sig+ratf[i]*ratf[i];
    }
avg=avg/1800.0;
sig=sqrt((sig-1800.0*avg*avg)/1800.0);
nopts=1800;
printf("Low Freq  nopts=%d\n",nopts);
printf("       avg=%f  sig=%f  relsig=%f\n",avg,sig,sig/avgdr);

avg=0;
sig=0;
for(i=0;i<1800;i++) /* calculate statistics */
    {
    admax[i]=ratn[i]-ratf[i];
    avg=avg+admax[i];
    sig=sig+admax[i]*admax[i];
    }
avg=avg/1800.0;
sig=sqrt((sig-1800.0*avg*avg)/1800.0);
nopts=1800;
printf("High Freq  nopts=%d\n",nopts);
printf("       avg=%f  sig=%f  relsig=%.\n",avg,sig,sig/avgdr);

/*********** parabola settings*********/
/*  bflg=2;
    if(gdnf<=(0.05-1062.5*sig*sig))
        {
```

```
            bflg=1;
            if(gdnf<=(0.04-437.5*sig*sig))
                {
                bflg=0;
                }
            }
*/
      /*********** ellipse limits ************/
      bflg=0;
      if((sig*sig/(aeg*aeg)+gdnf*gdnf/(beg*beg))>1.000001) bflg=bflg+1;
      if((sig*sig/(aeb*aeb)+gdnf*gdnf/(beb*beb))>1.000001) bflg=bflg+2;
      /**** 0=good, 1=unknown, 2=indeterminate, 3=bad ****/

/*************** end read bottle data *************/
             fclose(flp);

sound(1600);
        delay(300);
        nosound();
        delay(200);
        sound(1600);
        delay(300);
        nosound();
        printf("!!!!! Press 'd' to display data !!!!!\n");

chr=' ';
        while((chr!='d')&&(chr!='D'))
            {
            chr=getch();
            }
        cmnd=' ';
        gdrv=EGA;
        gmod=EGAHI;
        detectgraph(&gdrv,&gmod);
        printf("drv=%d   mode=%d\n",gdrv,gmod);
        initgraph(&gdrv,&gmod,"");

hg=480;/*height of graph  ega=350   vga=480 */
        sg=100;/* graph scale   ega=70 vga=100 */ setcolor(WHITE);
        line(80,hg-50,620,hg-50);
        line(80,hg-50,80,hg-50-4*sg);
        for(i=0;i<=12;i++)
            {
            line(80+45*i,hg-50,80+45*i,hg-45);
            }
        for(i=0;i<=8;i++)
            {
            line(75,hg-(50+i*sg/2),80,hg-(50+i*sg/2));
            }
        settextstyle(0,0,1);
        setcolor(10);
        outtextxy(350-44,hg-25,"ANGLE (DEG)");
        setcolor(WHITE);
        outtextxy(50,hg-12,"< Press Any Key to Stop SOUND >");
        outtextxy(80-4,hg-40,"0");
        outtextxy(125-8,hg-40,"30");
        outtextxy(170-8,hg-40,"60");
        outtextxy(215-8,hg-40,"90");
        outtextxy(260-12,hg-40,"120");
```

```
outtextxy(305-12,hg-40,"150");
outtextxy(350-12,hg-40,"180");
outtextxy(395-12,hg-40,"210");
outtextxy(440-12,hg-40,"240");
outtextxy(485-12,hg-40,"270");
outtextxy(530-12,hg-40,"300");
outtextxy(575-12,hg-40,"330");
outtextxy(620-12,hg-40,"360");

setcolor(14);
outtextxy(480,5,flnm);
outtextxy(480,15,runnu);

setcolor(WHITE);
outtextxy(26,hg-50-4,"-0.050");
outtextxy(26,hg-50-1*sg/2-4,"-0.025");
outtextxy(34,hg-50-2*sg/2-4,"0.000");
outtextxy(34,hg-50-3*sg/2-4,"0.025");
outtextxy(34,hg-50-4*sg/2-4,"0.050");
outtextxy(34,hg-50-5*sg/2-4,"0.075");
outtextxy(34,hg-50-6*sg/2-4,"0.100");
outtextxy(34,hg-50-7*sg/2-4,"0.125");
outtextxy(34,hg-50-8*sg/2-4,"0.150");

setcolor(10);
outtextxy(15,100,"%");
outtextxy(15,120,"P");
outtextxy(15,130,"O");
outtextxy(15,140,"L");
outtextxy(15,160,"C");
outtextxy(15,170,"H");
outtextxy(15,180,"A");
outtextxy(15,190,"N");
outtextxy(15,200,"G");
outtextxy(15,210,"E");

yoff=-0.05;

/******** major stress band ******/
ptavg=(int)(50.5+(avgdr-yoff)*sg/0.05);
ptsig=(int)(0.5+0.030*sg/0.05);
setcolor(8);
for(i=-ptsig;i<=2*ptsig;i++)
    {
    line(82,hg-(ptavg+i),620,hg-(ptavg+i));
    } taa=aeg*aeg*(1-gdnf*gdnf/(beg*beg));
if(taa<0)
    {
    ptsig=0;
    }else{
    ptsig=(int)(0.5+(sqrt(taa))*sg/0.05);
    }
/*    ptsig=(int)(0.5+0.004*sg/0.05);*/
setcolor(1);
for(i=-ptsig;i<=ptsig;i++)
    {
    line(82,hg-(ptavg+i),620,hg-(ptavg+i));
    } ptsig=(int)(0.5+sig*sg/0.05);
setcolor(12);
for(i=0;i<108;i++)
    {
    line(83+i*5,hg-(ptavg-ptsig),83+i*5,hg-(ptavg+ptsig));
    }
```

```c
setcolor(15);
line(80,hg-ptavg,620,hg-ptavg);

ptemp=(int)(50.5+(adrat[0]-yoff)*sg/0.05);
xpixl=80;
for(i=1;i<1800;i++)
    {
    setcolor(13);
    xpix=(int)(0.5+80+i*(360.0/1800)*(1.5));
    ptmp=(int)(50.5+(adrat[i]-yoff)*sg/0.05);
    line(xpixl,hg-ptemp,xpix,hg-ptmp);
    ptemp=ptmp;
    xpixl=xpix;
    } ptemp=(int)(50.5+(ratn[0]-yoff)*sg/0.05);
xpixl=80;
setcolor(11);
for(i=1;i<1800;i++)
    {
    xpix=(int)(0.5+80+i*(360.0/1800)*(1.5));
    ptmp=(int)(50.5+(ratn[i]-yoff)*sg/0.05);
    line(xpixl,hg-ptemp,xpix,hg-ptmp);
    ptemp=ptmp;
    xpixl=xpix;
    } ptemp=(int)(50.5+(ratf[0]-yoff)*sg/0.05);
xpixl=80;
setcolor(15);
for(i=1;i<1800;i++)
    {
    xpix=(int)(0.5+80+i*(360.0/1800)*(1.5));
    ptmp=(int)(50.5+(ratf[i]-yoff)*sg/0.05);
    line(xpixl,hg-ptemp,xpix,hg-ptmp);
    ptemp=ptmp;
    xpixl=xpix;
    } for(i=0;i<1800;i++)
    {
    ratf[i]=ratn[i]-ratf[i]+avgdr;
    }
ptemp=(int)(50.5+(ratf[0]-yoff)*sg/0.05);
xpixl=80;
setcolor(10);
for(i=1;i<1800;i++)
    {
    xpix=(int)(0.5+80+i*(360.0/1800)*(1.5));
    ptmp=(int)(50.5+(ratf[i]-yoff)*sg/0.05);
    line(xpixl,hg-ptemp,xpix,hg-ptmp);
    ptemp=ptmp;
    xpixl=xpix;
    } settextstyle(0,0,1);
setcolor(4);
if(pdflg==1) { outtextxy(350-112,hg-75,"POINT DEFECTS");}
if(msflg==1) { outtextxy(350+8,hg-75,"MAJOR STRESS AREA");} cmnd='';
settextstyle(0,0,2);
while(cmnd=='')
```

```
{
if(bflg==0)
    {
    setcolor(10);
    outtextxy(350-88,hg-65,"BOTTLE GOOD");
    sound(1600);
    }
if(bflg==1)
    {
    setcolor(2);
    outtextxy(350-112,hg-65,"BOTTLE UNKNOWN");
    sound(900);
    }
if(bflg==2)
    {
    setcolor(2);
    outtextxy(350-120,hg-65,"BOTTLE MARGINAL");
    sound(900);
    }
if(bflg==3)
    {
    setcolor(12);
    outtextxy(350-80,hg-65,"BOTTLE BAD");
    sound(660);
    }
delay(500);
if(bflg==0)
    {
    setcolor(2);
    outtextxy(350-88,hg-65,"BOTTLE GOOD");
    nosound();
    }
if(bflg==1)
    {
    setcolor(4);
    outtextxy(350-112,hg-65,"BOTTLE UNKNOWN");
    nosound();
    }
if(bflg==2)
    {
    setcolor(4);
    outtextxy(350-120,hg-65,"BOTTLE MARGINAL");
    nosound();
    }
if(bflg==3)
    {
    setcolor(4);
    outtextxy(350-80,hg-65,"BOTTLE BAD");
    sound(200);
    }
delay(500);
if(kbhit()!=0)
    {
    cmnd=getch();
/*     setcolor(0);
    outtextxy(350-88,hg-65,"BOTTLE GOOD");
    outtextxy(350-120,hg-65,"BOTTLE MARGINAL");
    outtextxy(350-80,hg-65,"BOTTLE BAD");
    if(cmnd=='0') {bflg=0;}
    if(cmnd=='1') {bflg=1;}
    if(cmnd=='2') {bflg=2;}
    */
    }
} nosound();
settextstyle(0,0,1);
```

```c
        setcolor(0);
        outtextxy(50,hg-12,"< Press Any Key to Stop SOUND >");
        setcolor(15);
        outtextxy(50,hg-12,"< Press 'M' for Menu, 'S' for Spectrum >");
        cmnd='';
        while(((cmnd!='m')&&(cmnd!='M'))&&((cmnd!='s')&&(cmnd!='S')))
           {
           cmnd=getch();
           }
        restorecrtmode();
        if((cmnd=='s')||(cmnd=='S'))
           {
           cmnd=' ';
/**************** plot fft **********************/
/************************************************/
        gdrv=EGA;
        gmod=EGAHI;
        detectgraph(&gdrv,&gmod);
        printf("drv=%d   mode=%d\n",gdrv,gmod);
        initgraph(&gdrv,&gmod,"");

hg=480;/*height of graph ega=350  vga=480 */
        sg=100;/* graph scale   ega=70 vga=100 */ setcolor(7);
/****** grid lines ********/
        for(i=1;i<=10;i++)
           {
           for(j=0;j<=32;j++)
              {
              line(80+54*i,hg-52-(j*sg)/8,80+54*i,hg-48-(j*sg)/8);
              }
           }
        for(i=1;i<=8;i++)
           {
           for(j=0;j<=40;j++)
              {
              line(78+(54*j)/4,hg-(50+i*sg/2),82+(54*j)/4,hg-(50+i*sg/2)
              }
           } setcolor(WHITE);
/********** axii *******************/
        line(80,hg-50,620,hg-50);
        line(80,hg-50,80,hg-50-8*sg);

/******** horizontal axis tic marks ******/
        for(i=0;i<=10;i++)
           {
           line(80+54*i,hg-50,80+54*i,hg-45);
           }

/******* vertical axis tic marks **********/
        for(i=0;i<=8;i++)
           {
           line(75,hg-(50+i*sg/2),80,hg-(50+i*sg/2));
           } settextstyle(0,0,1);
        setcolor(10);
        outtextxy(350-48,hg-20,"FREQ (1/REV)");
        setcolor(13);
        outtextxy(80-4,hg-40,"0");
        outtextxy(134-12,hg-40,"100");
        outtextxy(188-12,hg-40,"200");
        outtextxy(242-12,hg-40,"300");
```

```
    outtextxy(296-12,hg-40,"400");
    outtextxy(350-12,hg-40,"500");
    outtextxy(404-12,hg-40,"600");
    outtextxy(458-12,hg-40,"700");
    outtextxy(512-12,hg-40,"800");
    outtextxy(566-12,hg-40,"900");
    outtextxy(620-16,hg-40,"1000");

setcolor(12);
    outtextxy(80-4,hg-30,"0");
    outtextxy(134-8,hg-30,"20");
    outtextxy(188-8,hg-30,"40");
    outtextxy(242-8,hg-30,"60");
    outtextxy(296-8,hg-30,"80");
    outtextxy(350-12,hg-30,"100");
    outtextxy(404-12,hg-30,"120");
    outtextxy(458-12,hg-30,"140");
    outtextxy(512-12,hg-30,"160");
    outtextxy(566-12,hg-30,"180");
    outtextxy(620-12,hg-30,"200");

setcolor(14);
    outtextxy(480,5,flnm);
    outtextxy(480,15,runnu);

setcolor(WHITE);
    outtextxy(34,hg-50-4," -180");
    outtextxy(34,hg-50-1*sg/2-4," -160");
    outtextxy(34,hg-50-2*sg/2-4," -140");
    outtextxy(34,hg-50-3*sg/2-4," -120");
    outtextxy(34,hg-50-4*sg/2-4," -100");
    outtextxy(34,hg-50-5*sg/2-4," -80");
    outtextxy(34,hg-50-6*sg/2-4," -60");
    outtextxy(34,hg-50-7*sg/2-4," -40");
    outtextxy(34,hg-50-8*sg/2-4," -20");

setcolor(10);
    outtextxy(15,100,"M");
    outtextxy(15,110,"A");
    outtextxy(15,120,"G");
    outtextxy(15,130,"N");
    outtextxy(15,140,"I");
    outtextxy(15,150,"T");
    outtextxy(15,160,"U");
    outtextxy(15,170,"D");
    outtextxy(15,180,"E");
    outtextxy(15,200,"d");
    outtextxy(15,210,"B");

yoff=-180;

i=0;
    mag=sqrt((*(d+2*i))*(*(d+2*i))+(*(d+2*i+1))*(*(d+2*i+1)))/nfft;
    mag=20.0*log10(mag);
    ptemp=(int)(50.5+(mag-yoff)*sg/40.0);
    xpixl=80;
    for(i=1;i<=1000;i++)
    {
        setcolor(13);
        xpix=(int)(0.5+80+i*(360.0/1000.0)*(1.5));
        mag=sqrt((*(d+2*i))*(*(d+2*i))+(*(d+2*i+1))*(*(d+2*i+1)))/nff
        mag=20.0*log10(mag);
```

```
            ptmp=(int)(50.5+(mag-yoff)*sg/40.0);
            line(xpixl,hg-ptemp,xpix,hg-ptmp);
            ptemp=ptmp;
            xpixl=xpix;
            )

/********** plot times 5 expansion of freq axis **********/
        i=0;
        mag=sqrt((*(d+2*i))*(*(d+2*i))+(*(d+2*i+1))*(*(d+2*i+1)))/nfft;
        mag=20.0*log10(mag);
        ptemp=(int)(50.5+(mag-yoff)*sg/40.0);
        xpixl=80;
        for(i=1;i<=200;i++)
            (
            setcolor(12);
            xpix=(int)(0.5+80+i*(360.0/200.0)*(1.5));
            mag=sqrt((*(d+2*i))*(*(d+2*i))+(*(d+2*i+1))*(*(d+2*i+1)))/nf
            mag=20.0*log10(mag);
            ptmp=(int)(50.5+(mag-yoff)*sg/40.0);
            line(xpixl,hg-ptemp,xpix,hg-ptmp);
            ptemp=ptmp;
            xpixl=xpix;
            )

/********** plot times 25 expansion of freq axis **********/
        i=0;
        mag=sqrt((*(d+2*i))*(*(d+2*i))+(*(d+2*i+1))*(*(d+2*i+1)))/nfft
        mag=20.0*log10(mag);
        ptemp=(int)(50.5+(mag-yoff)*sg/40.0);
        xpixl=80;
        for(i=1;i<=40;i++)
            (
            setcolor(11);
            xpix=(int)(0.5+80+i*(360.0/40.0)*(1.5));
            mag=sqrt((*(d+2*i))*(*(d+2*i))+(*(d+2*i+1))*(*(d+2*i+1)))/n:
            mag=20.0*log10(mag);
            ptmp=(int)(50.5+(mag-yoff)*sg/40.0);
            line(xpixl,hg-ptemp,xpix,hg-ptmp);
            ptemp=ptmp;
            xpixl=xpix;
            )

/*********** plot area above dB ***********/
        for(k=0;k<=20;k++)
            (
            ylsf[k]=0.0;
            )
        for(i=1;i<=1000;i++)
            (
            mag=sqrt((*(d+2*i))*(*(d+2*i))+(*(d+2*i+1))*(*(d+2*i+1)))/n:
            mag=20.0*log10(mag);
            for(k=0;k<=20;k++)
                (
                if(mag>(-5.0*k)) ylsf[k]=ylsf[k]+mag+5.0*k;
                )
            )
        i=0;
        ptemp=(int)(50.5+(10.0*sqrt(ylsf[i]))*sg/200.0);
        xpixl=80;
        for(i=1;i<=20;i++)
            (
            setcolor(10);
            xpix=(int)(0.5+80+5.0*i*(360.0/100.0)*(1.5));
            ptmp=(int)(50.5+(10.0*sqrt(ylsf[i]))*sg/200.0);
            line(xpixl,hg-ptemp,xpix,hg-ptmp);
            ptemp=ptmp;
            xpixl=xpix;
            )
```

```c
   settextstyle(0,0,1);
   setcolor(4);
   if(pdflg==1) { outtextxy(350-112,hg-75,"POINT DEFECTS");}
   if(msflg==1) { outtextxy(350+8,hg-75,"MAJOR STRESS AREA");}
cmnd='';
settextstyle(0,0,2);
while(cmnd=='')
   {
   delay(500);
   if(bflg==0)
      {
      setcolor(2);
      outtextxy(350-88,hg-65,"BOTTLE GOOD");
      nosound();
      }
   if(bflg==1)
      {
      setcolor(4);
      outtextxy(350-112,hg-65,"BOTTLE UNKNOWN");
      nosound();
      }
   if(bflg==2)
      {
      setcolor(4);
      outtextxy(350-120,hg-65,"BOTTLE MARGINAL");
      nosound();
      }
   if(bflg==3)
      {
      setcolor(4);
      outtextxy(350-80,hg-65,"BOTTLE BAD");
      sound(200);
      }
   delay(500);
   cmnd='1';
   if(kbhit()!=0)
      {
      cmnd=getch();
/*       setcolor(0);
      outtextxy(350-88,hg-65,"BOTTLE GOOD");
      outtextxy(350-120,hg-65,"BOTTLE MARGINAL");
      outtextxy(350-80,hg-65,"BOTTLE BAD");
      if(cmnd=='0') {bflg=0;}
      if(cmnd=='1') {bflg=1;}
      if(cmnd=='2') {bflg=2;}
      */
      }
   } nosound();
settextstyle(0,0,1);
setcolor(15);
outtextxy(50,hg-12,"< Press 'M' for Menu >");
cmnd='';
while((cmnd!='m')&&(cmnd!='M'))
   {
   cmnd=getch();
   }
   restorecrtmode();
   }/******* end of spsetrum plot ******/
   cmnd=' ';

}
```

```
exit(0);
)/***** end of main *****/

/*************************************************/
/********* Functions in file botf40.c *********/
/*************************************************/
/****** other functions in file spline2.c ******/
/*************************************************/
```

To better understand operation of the system in a typical application, a step by step discussion of system operation and data reduction is presented as follows A. The analyzer 52 is rotated so that maximum light intensity is achieved on the photodetector 55, with the analyzer 52 being aligned with the plane of light polarization produced by the polarized light source assembly 30. Typically, the rotational step resolution of the analyzer rotation assembly 60 for rotating analyzer 52 is about 0.75°. The exact rotational step size is not critical but it should be fine enough so that the polarizer can be rotated fairly close to the true maximum.

B. The light source 32 intensity is varied until the measured plane polarized light output is at a set value approximately equal to 75% of the full scale output. This is done so that consecutive runs will be taken at the same light intensity in order increasing consistency of stress measurements.

C. The analyzer 52 is rotated 360° four times and the detected light output measured as a function of angle in order to determine the two maxima and two minima.

D. The analyzer 52 is rotated 360° and the intensity is measured to determine the background transmission and polarization with no bottle present.

E. The periscope 46 is raised and the bottle 12 is placed onto the platter 22 and held firmly in position. The periscope 46 is then lowered into the bottle cavity 16 of the bottle 12 so that the plane polarized light will pass through the bottle wall and fall onto the photodetector.

F. The analyzer 52 is rotated to a first light intensity maxima and the light intensity is measured as a function of bottle angle as the bottle is rotated 360° by rotating the bottle platter. The bottle is rotated in 0.2° steps. After rotating one step the bottle is stopped and the light intensity is measured. The bottle is then rotated the next step. The speed of rotation is approximately 10 milliseconds per step. The step size and rotation speed are set such that the detector electronics will have time to settle and so that the angular resolution will be fine enough to measure the variations in the bottle. The exact speed and resolution can be chosen to to give a good signal on the particular bottle of interest.

G. The analyzer 52 is rotated to the first light intensity minima and the intensity as a function of bottle angle is again measured.

H. The analyzer 52 is then rotated to the second light intensity maxima and second minima and the intensity angular function si measured as before for each.

I. The bottle is removed and the background is measured again.

J. The polarization intensity is calculated for each point measured around the bottle. For each point, i, the polarization intensity, $P(i)=[Imax(i)-Imin(i)]/[Imax(i)+Imin(i)]$, where: $Imax(i)$ is the average of the first and second maxima and $Imin(i)$ is the average of the first and second minima at point i.

K. Next the change in polarization is calculated for each point around the bottle, $Rp(i)=P(i)/P(n)$, where $P(n)$ is the polarization with no bottle present. With the current system changes in polarization can be measured to better than one part in 10,000 or better than 0.01%. This data is saved in a data file along with other information such as time, data, comments, background level, average level etc., L. The slope of the relation $Rp(i)$ as a function of angle is examined and areas of relatively large changes of slope are categorized as point defects. These regions are eliminated from the data by replacing them with a straight line going from the point proceeding the region in question to the first point after that region to give $Rpm(i)$.

M. The low frequency portion of the relation $Rp(i)$ is calculated be applying a digital lowpass filter to the data with the point defects removed, $Rrm(i)$. The cutoff of this filter is currently 200 points. This is equivalent to a spatial wave length of 40°. $Rlf(i)$ will be used to reference this low frequency portion of the relation.

N. The spatial spectral energy of $Rrm(i)$ around the bottle is calculated by determining the root-mean-square of the data with the point defects removed. The high frequency portion of the relation is found by subtraction the low frequency portion, $Rlf(i)$, from the whole, $Rrm(i)$. The energy for this relation, $Rhf(i)$, containing spatial frequencies less than 40° in extent (high frequency stress) is determined by using root-mean-square relation.

Figure 2:
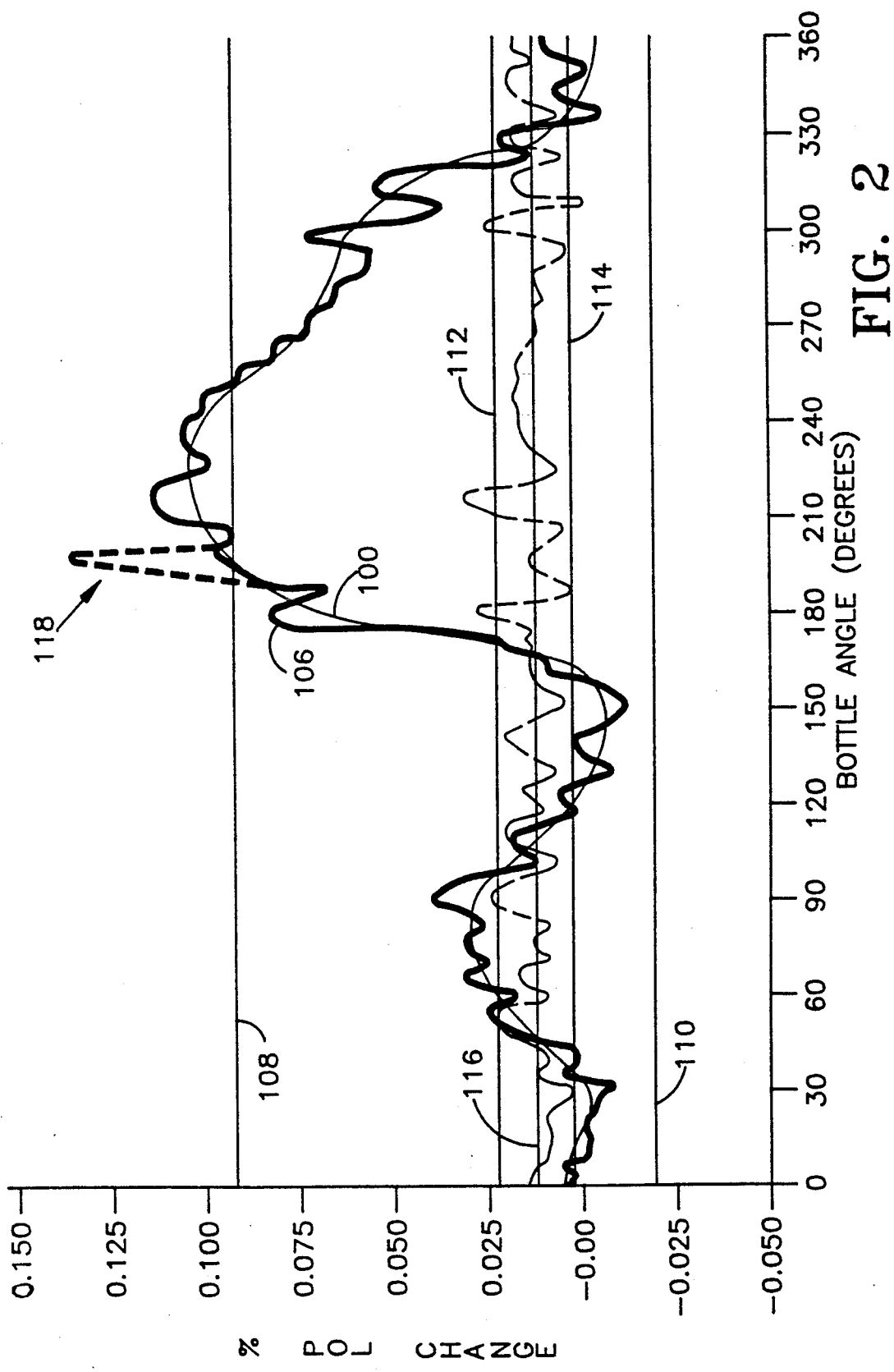
FIG. 2 is a representative graphic output presented by a computer display monitor to indicate stress levels at a predetermined height around a bottle, with accept-/reject limits being indicated as horizontal lines.

M. The various forms of $Rp(i)$ are plotted on the computer monitor for realtime examination by an operator. These include the total $Rp(i)$, $Rp(i)$ with point defects moved $Rrm(i)$, the low frequency component ($Rlf$) of $Rrm(i)$ and the high frequency component ($Rhf$) of $Rrm(i)$. FIG. 2 illustrates this display on a computer. Although not shown, the display can be color coded to enhance viewability.

Figure 3:
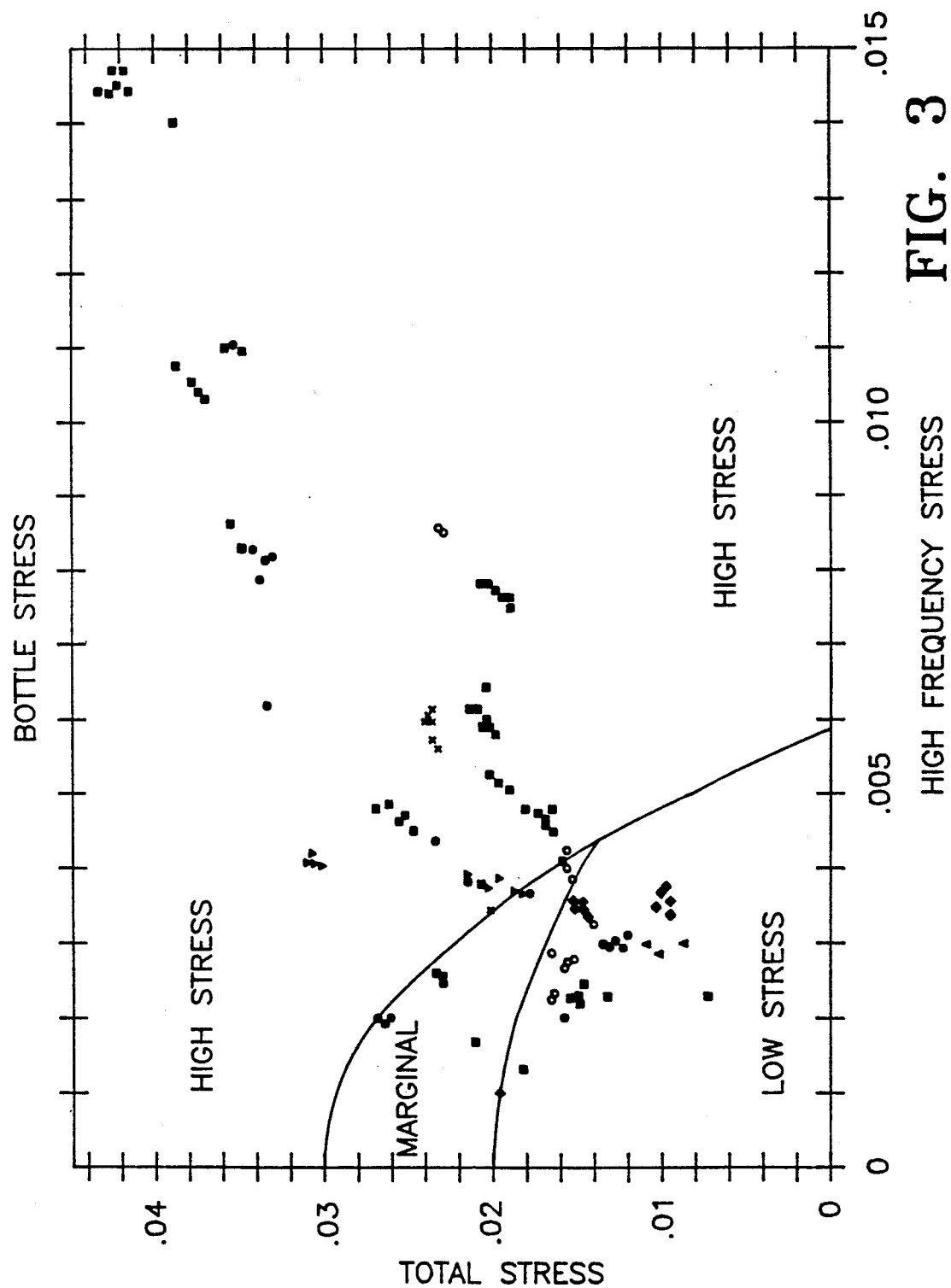
FIG. 3 is a representative graphic output presented by a computer display monitor to indicate low, high, and marginal stress regions for samples of bottles taken from several experimental lots.

O. The high frequency energy and total stress energy are plotted on a graph such as illustrated in FIG. 3 of total stress versus high frequency stress and compared to standard ranges to indicate the proper annealing. In general the smaller the high frequency stresses the better the annealing. However this is dependent on the resin and the molding process used. There is also a relationship between the total and high frequency stresses. FIG. 3 shows this relationship, with selected experimental bottles stress levels plotted and the regions used to determine the proper degree of annealing.

Although the invention has been described in detail with reference to certain preferred embodiments and specific examples, variations and modifications exist within the scope and spirit of the invention as defined in the following claims.

We claim:

1. A bottle stress analysis system using polarized light for determining stress levels of a transparent plastic bottle, the transparent plastic bottle having a bottle wall that defines a bottle cavity, the bottle stress analysis system comprising
   a rotation assembly for rotating the bottle,
   a polarized light source assembly insertible into the bottle cavity to direct plane polarized light through the bottle wall
   an analyzer assembly positioned outside the bottle for measuring intensity of light passing through the bottle wall, the analyzer assembly having a polarization analyzer positioned to transmit the light to a photodetector,
   means for rotating one of the polarized light source and the analyzer to determine maximum and minimum polarized light intensity at the photodetector, and
   means for correlating stress levels from the maximum and minimum polarized light intensity measurements, the correlating means comprising means for determining change in polarization Rp(i) for each measurement and means for determining high frequency components of Rp(i) to determine annealing conditions of the bottle.

2. The bottle stress analysis system of claim 1 wherein the rotation assembly further comprises a rotatable platter configured to support the bottle.

3. The bottle stress analysis system of claim 2 further comprising a platter stepper motor connected to the platter to rotate the platter a predetermined angular distance and briefly maintain a stationary position until maximum and minimum polarized light intensity is determined.

4. The bottle stress analysis system of claim 3 further comprising a computer control assembly for automatically controlling operation of the platter stepper motor, the computer control assembly controlling the angular distance through which the platter is rotated, and the duration the stationary position is maintained before further rotation.

5. The bottle stress analysis system of claim 1 wherein the polarized light source assembly further comprises a periscope insertible through a neck of the bottle into the bottle cavity, the periscope holding a light source and a polarizer for transmitting plan polarized light.

6. The bottle stress analysis system of claim 5 wherein the polarizer is positioned to transmit plane polarized light at a 45° angle with respect to an axis of symmetry of the bottle.

7. The bottle stress analysis system of claim 5 wherein the light source further comprises a light emitting diode connected to a light source intensity control to vary intensity of light emitted by the diode.

8. The bottle stress analysis system of claim 7 wherein the light source intensity control is connected to a computer control assembly for automatically controlling operation of the light source intensity control.

9. The bottle stress analysis system of claim 7 further comprising a lens for focusing light emitted by the light emitting diode, and a mirror for reflecting converging, plane polarized light toward a stress analysis point on the bottle wall coincident with the focal point.

10. The bottle stress analysis system of claim 1 wherein the analyzer assembly further comprises a lens for focusing polarized light passing through the polarization onto the photodetector.

11. The bottle stress analysis system of claim 10 wherein the photodetector is configured to have a varying electric current in response to variations in light intensity, and further comprising an electrical converter for converting the current to an electrical voltage and an electrical amplifier for amplifying the electrical voltage.

12. The bottle stress analysis system of claim 11 further comprising a computer control assembly having an analog to digital converter for converting electrical voltage output of the amplifier into computer readable digital format.

13. The bottle stress analysis system of claim 1 wherein the rotating means further comprises an analyzer rotation assembly for rotating the polarization analyzer relative to a fixed plane of polarization of light emitted by the polarized light source assembly.

14. The bottle stress analysis system of claim 13 further comprising an analyzer motor means connected to the polarization analyzer to rotate the polarization analyzer a predetermined angular distance and briefly maintain a stationary position until maximum and minimum polarized light intensity is determined.

15. The bottle stress analysis system of claim 14 further comprising a computer control assembly for automatically controlling operation of the analyzer stepper motor, the computer control assembly controlling the angular distance through which the polarization analyzer is rotated, and the duration the stationary position is maintained before further rotation.

16. A method for determining stress levels of a transparent plastic bottle, the method comprising the steps of
   providing a polarized light source assembly to direct polarized light toward an analyzer assembly positioned for measuring intensity of the polarized light, the analyzer assembly having a polarization analyzer positioned to transmit the light to a photodetector to determine maximum and minimum polarized light intensity at the photodetector as the polarization analyzer is rotated relative to the polarized light source assembly,
   determining maximum and minimum light intensities as the polarization analyzer is rotated relative to the polarized light source,
   positioning a bottle wall of a transparent plastic bottle between the polarized light source and the analyzer assembly,
   redetermining maximum and minimum light intensities as the polarization analyzer is rotated relative to the polarized light source,
   determining polarization change from the maximum and minimum measured light intensities to obtain a function Rp(i) related to stress levels in the bottle, and
   examining a slope of the function Rp(i) as a function of angle and eliminating high slope data as point defects before determining high frequency components of Rp(i) to determine annealing conditions of the bottle.

17. The method of claim 16 further comprising the steps of
inserting the polarized light source assembly into the bottle
rotating the bottle a predetermined angular distance, and
maintaining a stationary position until maximum and minimum polarized light intensity is determined.

* * * * *